United States Patent [19]
Dill et al.

[11] Patent Number: 5,164,064
[45] Date of Patent: Nov. 17, 1992

[54] HPE CAPILLARY CARTRIDGE WITH EXPOSED RETRACTABLE CAPILLARY ENDS

[75] Inventors: Rand Dill, Corte Madera; Samuel Burd, Oakland, both of Calif.

[73] Assignee: Bio-Rad Laboratories, Inc., Hercules, Calif.

[21] Appl. No.: 686,644

[22] Filed: Apr. 17, 1991

[51] Int. Cl.$^5$ .................. G01N 27/26; B01D 57/02
[52] U.S. Cl. ........................ 204/299 R; 204/180.1
[58] Field of Search .............. 204/183.3, 299 R, 180.1

[56] References Cited

U.S. PATENT DOCUMENTS

| | | | |
|---|---|---|---|
| 4,906,344 | 3/1990 | Hjerten | 204/183.3 |
| 4,911,807 | 3/1990 | Burd | 204/183.3 |
| 4,985,129 | 1/1991 | Burd | 204/183.3 |
| 5,019,236 | 5/1991 | Young | 204/299 R |
| 5,037,523 | 8/1991 | Weinberger et al. | 204/299 R |

Primary Examiner—John Niebling
Assistant Examiner—John S. Starsiak, Jr.
Attorney, Agent, or Firm—Townsend and Townsend

[57] ABSTRACT

A capillary cartridge for high performance electrophoresis is constructed in two parts—an internal cooling block and an external housing, both constructed to permit sliding of the cooling block within the housing to provide two positions, one of which is a retracted position in which the exposed ends of the capillary, which protrude from the cooling block, are protected by the housing, and the other an extended position in which the exposed ends of the capillary extend beyond the cooling block for access for sample loading and connections to electrode buffers. An improved coolant flow channel inside the cartridge is also included.

13 Claims, 3 Drawing Sheets

HPE CAPILLARY CARTRIDGE WITH EXPOSED RETRACTABLE CAPILLARY ENDS

This invention relates to capillary electrophoresis, and in particular to cartridges which contain capillary tubes and which are designed for use in automated electrophoresis equipment.

BACKGROUND OF THE INVENTION

Capillary electrophoresis is a well known form of high performance electrophoresis (HPE) and a highly effective means of analyzing extremely small biological samples. The long separation path in a capillary permits the separation of a multitude of components in a single sample, including components which are closely related. The thin diameter of a capillary permits the use of a high voltage, which produces separations in a relatively short period of time. Furthermore, capillaries are particularly well suited for on-line detection of the separated species using a light beam passing through the capillary directly into a detector.

Capillary electrophoresis has been facilitated considerably by the use of cartridges to contain the capillaries. Cartridges eliminate the need for the operator to handle the capillary directly, and permit easy and secure connections with associated devices and apparatus such as electrode chambers, sample reservoirs and detection apparatus. Cartridges also offer means of cooling of the capillary. This is done in some cartridges by the contact of the capillary with heat-dissipating materials of extended surface areas, and in others by contact with a coolant circulating through the cartridge.

The ability of a cartridge to be easily and rapidly connected with and disconnected from its associated components is generally achieved at the cost of smooth and efficient fluid flow in and out of the cartridge. Since the capillary ends must be protected from breakage, the small internal diameter of the capillary is not continued through most fittings, and the result is dead space in the fitting. Dead space interferes with the loading of sample into the capillary as well as the elution and clearance of separated sample components from the capillary. Other problems include the cooling efficiency, notably the uniformity and continuity of coolant flow along the entire capillary length. Dead space in the coolant flow path and unequal coolant rates along the capillary length affect the response of the capillary to the coolant and the reliability and reproducibility of the results.

SUMMARY OF THE INVENTION

These and other problems are addressed by the present invention, which resides in a novel two-part capillary cartridge. The capillary ends extend outside the cartridge but are retracted when not in use and when the cartridge is not in contact with the sample, electrical and detection components. The two parts of the cartridge are joined in a sliding arrangement, and can be moved between a retracted position in which the exposed capillary ends are shielded from contact, and an extended position in which the capillary ends are accessible to electrode or sample chambers for the performance of electrophoresis.

Various details, features and preferred embodiments of the invention are described below.

BRIEF DESCRIPTION OF THE DRAWINGS

FIG. 4 is a cross section of the cooling block of FIG. 3, taken along the line 5—5 thereof.

DETAILED DESCRIPTION OF THE INVENTION AND PREFERRED EMBODIMENTS

Figure 1:
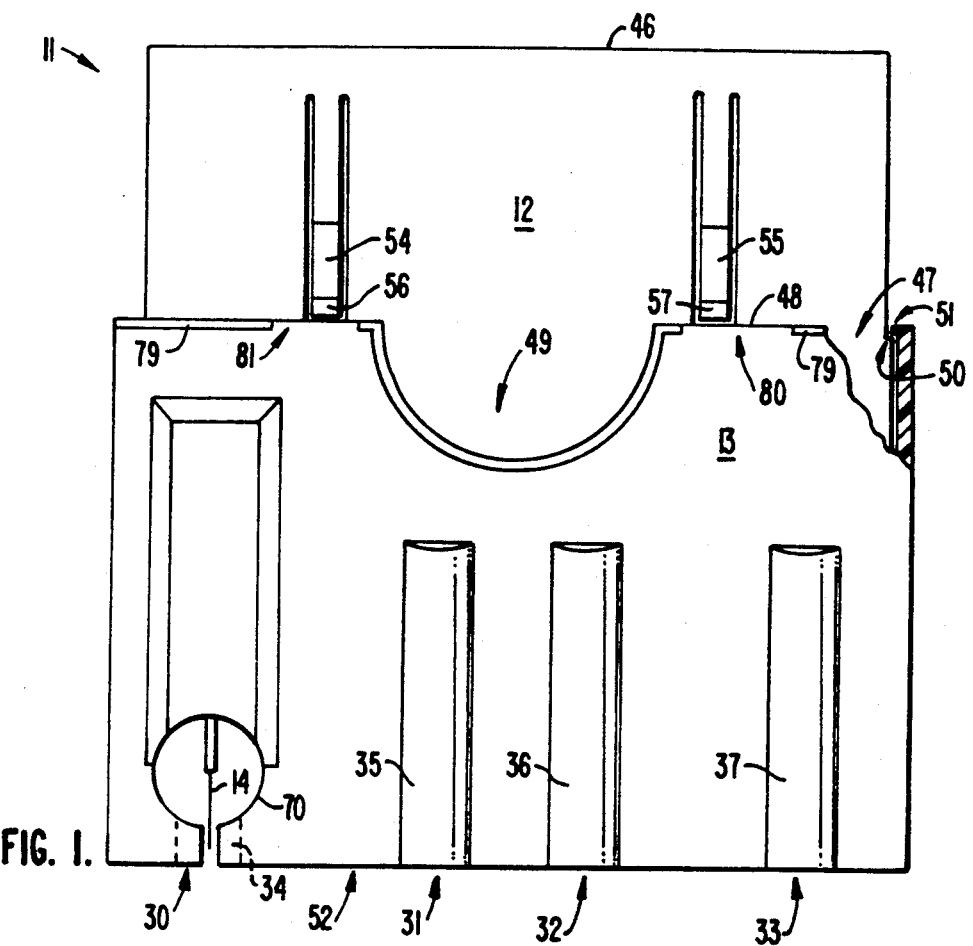
FIG. 1 is a front elevation of a capillary cartridge representing one illustrative embodiment of the present invention, with a section broken away to show a portion of the interior of the cartridge. The cartridge in this Figure is shown in the retracted position.

The invention in both its broadest sense and in the details of its preferred embodiments is best understood by examination of a single example. One such example is depicted in the drawings.

Figure 2:
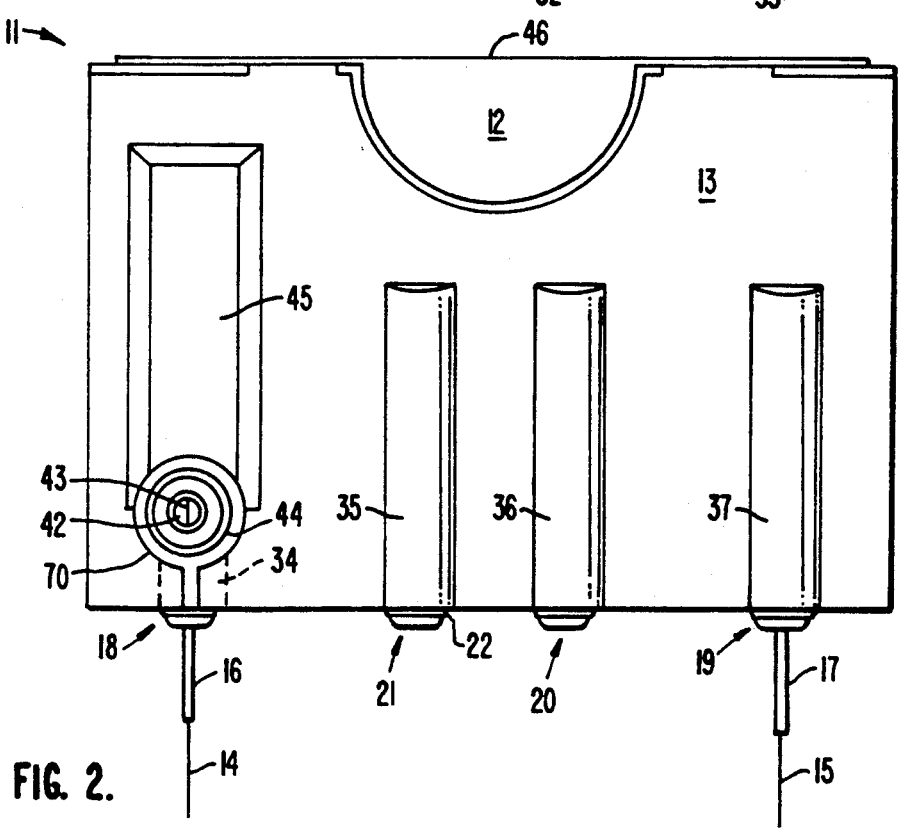
FIG. 2 is a front elevation of the capillary cartridge of FIG. 1 in the extended position.

The cartridge 11 of this example is shown in FIGS. 1 and 2, which show the cartridge in its retracted and extended positions, respectively. The two parts of the cartridge are a cooling block 12 and a housing 13, both generally rectangular in shape and having thicknesses (perpendicular to the plane of the Figures) which are considerably less than their heights and widths. A capillary (not visible in either Figure) is coiled inside the cooling block 12, the two ends of the capillary 14, 15, extending from the cooling block. As seen in the Figures, the term "retracted position" as it is used herein refers to the position in which the capillary ends 14, 15 are retracted into, and protected by, the housing. Likewise, the term "extended position" is used herein to indicate the position in which the capillary ends extend beyond the housing and are fully exposed for sample loading and electrical contact.

Each of the exposed capillary ends 14, 15 is further protected by a rigid support tube 16, 17 which stabilizes the capillary end and directs it straight downward. Each capillary is sealed inside the corresponding support tube to prevent leakage between the capillary and the support tube, and leakage around the support tube exterior is likewise prevented by sealing material, although these seals are not visible in the Figures.

Each of the support tubes, and hence the capillary ends, is secured into a mounting 18, 19, respectively, along the edge of the cooling block 12. Also along the same edge are two coolant ports 20, 21 which serve as inlet and outlet, respectively for liquid coolant passing through the cooling block. These ports communicate with the interior of a coolant flow channel inside the cooling block; this coolant flow channel is visible in FIG. 3 and will be discussed in detail below.

The capillary mountings 18, 19 and the coolant ports 20, 21 are all circular and all protrude from the end of the cooling block, and each is surrounded by an O-ring 22 or other type of resilient gasket material. With the cartridge in the extended position as shown in FIG. 2, the capillary ends 14, 15, the capillary mountings 18, 19 and the coolant ports 20, 21 also extend beyond the lower edge of the housing 13. When the cartridge is inserted into an instrument which contains electrical connections, buffer and sample reservoirs, coolant supply and circulation pump, light source and detector, and controls and programming for automated operation, these protruding mountings, ports and O-rings will each become engaged with mated ports, openings or seats to provide the necessary fluid communications between the instrument and the cartridge interior to permit temperature-controlled sample loading and electrophoresis. The O-rings seal against the sides of the bore in the ports or openings of the instrument and are further distorted by elevated pressure from the instrument, the combined effect being to prevent both the separation medium in the capillary and the coolant medium from leaking out.

As the cartridge 11 passes from the extended position to the retracted position (FIG. 1), the capillary ends, capillary mountings and coolant ports all pass through openings 30, 31, 32, 33 into the interior of the housing. Each such opening leads into an internal channel 34, 35, 36, 37 in the housing, each such channel being of sufficient diameter to permit the capillary mountings and coolant ports to travel along the length of the channel. In three of the four channels (35, 36 and 37), the coolant ports 20, 21 and one of the capillary mountings 19 abut the closed ends 38, 39, 40, respectively, of the channels at the upper end of their path of travel, preventing them from further upward movement. The closed ends thus serve as stops for the sliding travel of the cooling block 12 inside the housing 13 in the upward direction, according to the view shown in the Figures. The closed bottom edge 41 of the housing serves as a stop for sliding travel in the downward direction. Together, these stops prevent disengagement of the two parts of the cartridge.

Directly above the leftmost capillary mounting 18 in the view shown in FIG. 2 is an opening 42 for the passage of a light beam through the capillary 43 for purposes of solute detection. Further details of the opening, the internal capillary and the detection are given below. For the purposes of FIGS. 1 and 2, however, it is significant to note that the opening is surrounding by a raised cylindrical rim 44, with an identical rim on the opposite side, both of which protrude outward to a combined distance exceeding the thickness of the housing 13. To accommodate the travel of these raised rims when the cooling block is moved relative to the housing, the housing contains an expanded internal channel 45.

It will be noted from FIGS. 1 and 2 that the upper edge 46 of the cooling block protrudes from the housing through an opening 47 in the top edge 48 of the housing. The cooling block is readily moved into the extended position (FIG. 2) by pushing the cooling block down inside the housing. Likewise, the cooling block is moved from the extended position to the retracted position (FIG. 1) by pulling the cooling block upward. To facilitate this, the upper edge 48 of the housing has a central recessed portion or U-shaped cut-out 49 on both sides (only one side being visible in these Figures) which permits the user to manually grasp the cooling block to pull it upward.

It will also be noted in the cutaway section of FIG. 1 that the cooling block 12 has a shoulder 50 on its side edge. This shoulder abuts an inwardly protruding retaining rim 51 on the housing 13 extending toward the opening 47. The shoulder 50 and retaining rim 51 serve as a stop for the sliding travel of the cooling block 12 inside the housing 13 in the upward direction, according to the view shown in the Figures. The closed bottom edge 52 of the housing serves as a stop for sliding travel in the downward direction. Together, these stops prevent disengagement of the two parts of the cartridge.

FIG. 1 further depicts a pair of spring-loaded catches or stops 54, 55 on the cooling block 12. These catches are resilient tabs with lower ends 56, 57 which when relaxed protrude outwardly from the otherwise flat face of the cooling block, i.e., outwardly from the plane of the Figure. These protruding ends 56, 57 abut the upper edge 52 of the housing 13, i.e., the rim surrounding the opening 51, preventing the cooling block from slipping down into the housing or from being inadvertently pushed into or toward the extended position. Release of these catches is achieved by pressure on the protruding ends 56, 57 until they clear the rim sufficiently to pass into the opening 51. As will be explained in more detail below, these catches are released by pins in the instrument into which the cartridge is inserted, with the result that the exposed capillary ends will be extended from the housing only when the cartridge is installed in the instrument.

Figure 3:
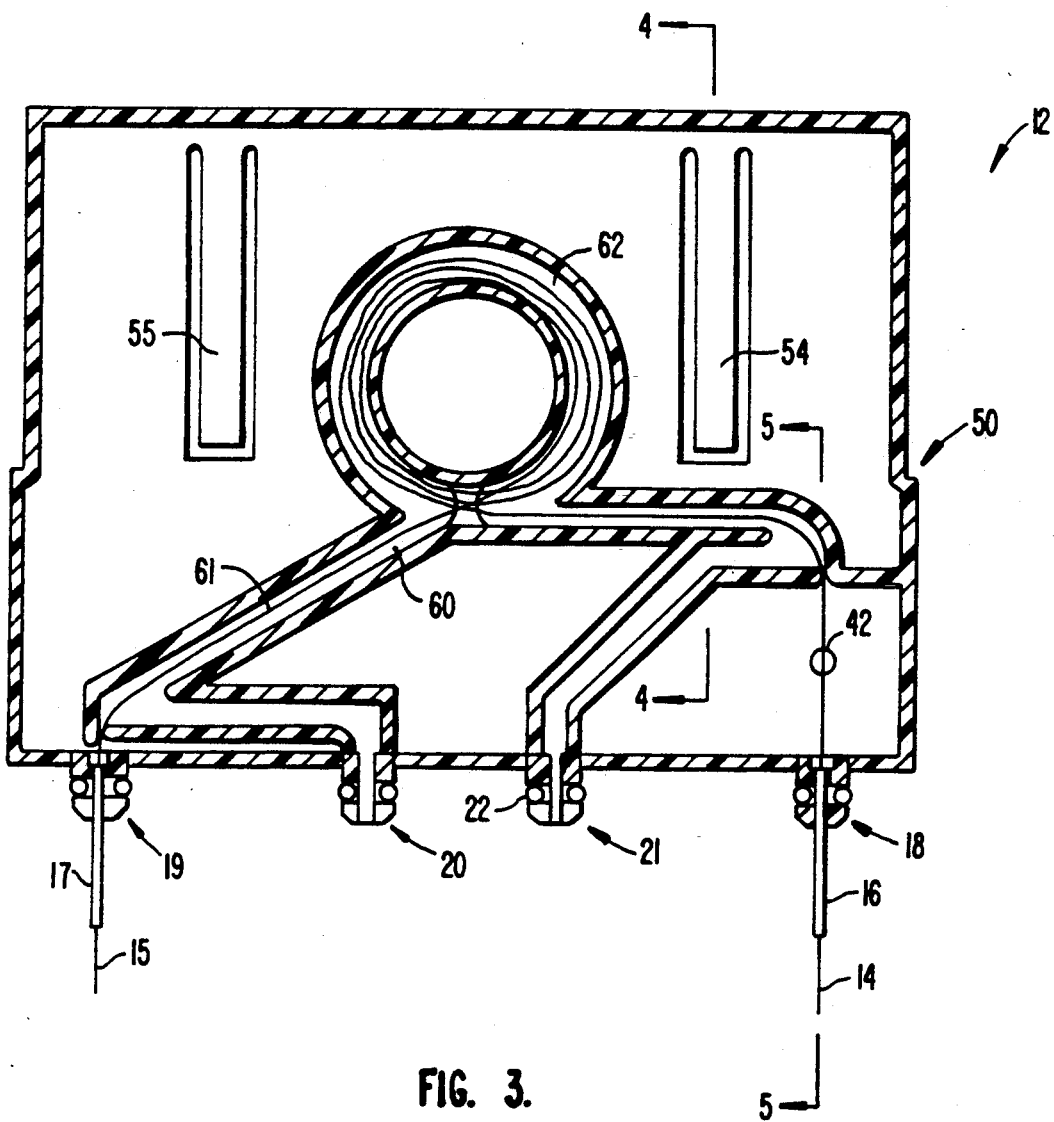
FIG. 3 is a cross section of the cooling block portion of the capillary cartridge of FIGS. 1 and 2.

Turning next to FIG. 3, the interior of the cooling block 12 is shown, facing in the reverse direction from that shown in FIGS. 1 and 2. Accordingly, the reverse side of the catches 54, 55 is shown. The interior of the cooling block is molded to form a coolant flow channel 60, which is a narrow channel of substantially constant width to accommodate the capillary 61, and containing a looped portion 62 to contain a coiled segment of the capillary, with the capillary coiled to form any number of loops as desired. The coolant flow channel 60 is fed with coolant fluid through the coolant inlet port 21, and coolant leaves through the coolant exit port 20. It will be noted that the coolant flow channel 60 is shaped to direct the coolant flow around the loop 62 with little or no dead volume in the flow path.

Sample loading will be performed at the inlet end 15 of the capillary, and the voltage will be applied such that electrophoretic migration will proceed from the inlet end 15 toward the outlet end 14. In proximity to the outlet end is the detection window 42, where on-line solute detection is conducted. The cooling block contains a matching window on its other face (not shown in this view), the windows being aligned to form a light path which passes through the capillary. When the cartridge is inserted in an instrument, the light path will be aligned with a light source and detector in the instrument for automated detection.

Figure 4:
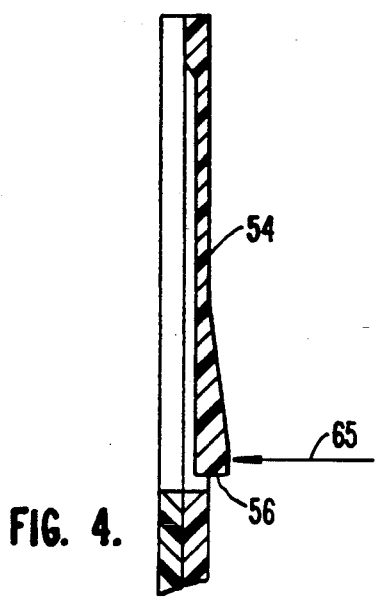
FIG. 4 is a cross section of the cooling block of FIG. 3, taken along the line 4—4 thereof.

The view in FIG. 4 is taken along the line 4—4 in FIG. 3, and shows a cross-section of the catch 54 with its protruding end 56. The catch is released by pressure on the protruding end in the direction of the arrow 65.

Figure 5:
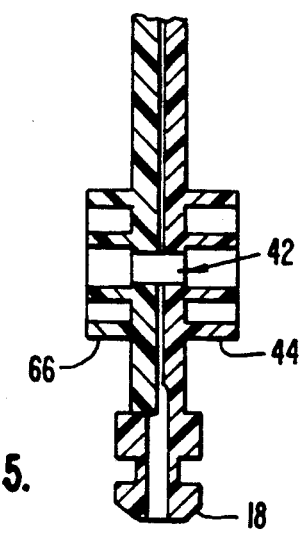
Figure 6:
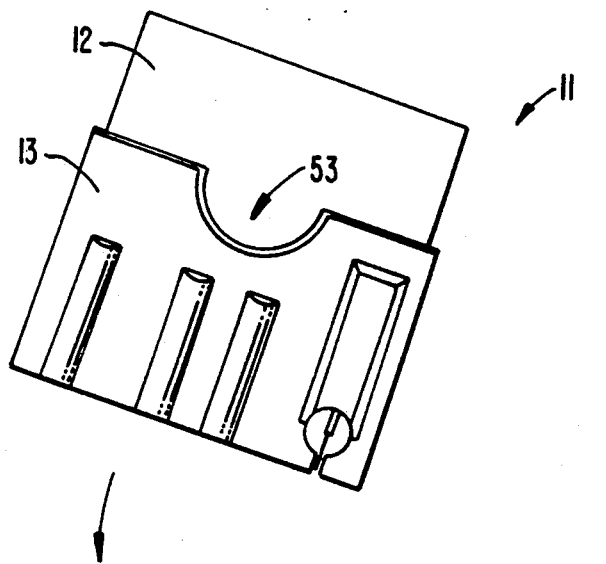
FIG. 6 is a front elevation of the capillary cartridge of the preceding Figures, shown together with an instrument providing fluid and electrical connections as well as a detection unit for use with the cartridge.
Figure 6:
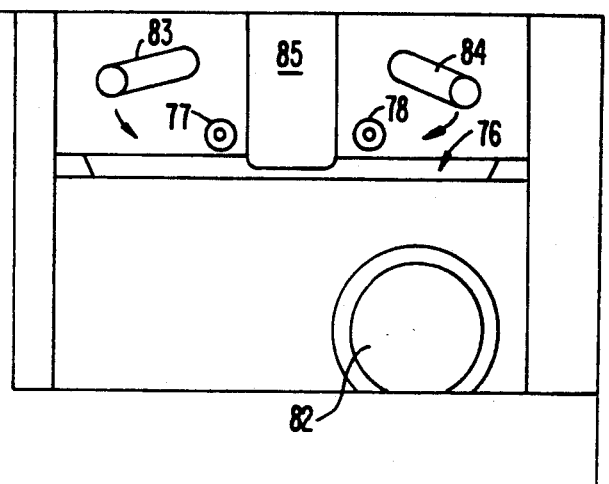

The view in FIG. 5 is taken along the line 5—5 in FIG. 3, with the capillary 14 and support tube 16 removed. Lenses (not shown) may be embedded in the walls of the cooling block on both sides of the light path opening 42.

The raised cylindrical rims 44, 66 on both sides of the cooling block surrounding the light path opening 42 serve to protect the lenses and also serve as means of securing the alignment of the light path opening with the light beam in the instrument when the cartridge is inserted. As indicted above, these cylindrical rims 44, 66 extend outward beyond the two flat faces of the housing when the cooling block is fully inserted into the housing such that the exposed capillary ends are in the extended position. The protruding rims are thus accessible for contact by cradle members in the instrument (not shown in the Figures herein), of complementary curvature. The engagement of the cylindrical rims by the cradle members is a means of assuring proper alignment of the capillary and lenses in the optical path inside the instrument.

With regard to the raised cylindrical rims and cradle members, it will be noted in FIGS. 1 and 2 that the housing 13 contains a window 70 through which the raised rim on one side of the cooling block will protrude, with a corresponding window on the other side of the housing (not visible in the Figure) for the raised rim on the other side. The surface of the housing 13 below the windows 70 is flat to permit the housing to slide down between the two opposing cradles which will then engage the sides of the protruding rims. This flat portion is in contrast to the raised external contours of the channels 35, 36, 37 and 45.

Turning finally to FIG. 5, the capillary cartridge 11 is shown poised for placement inside the instrument 75 which, as indicated above, houses components and connections for loading sample into the capillary, supplying a voltage to the capillary through electrode buffers, supplying coolant to the coolant flow channel surrounding the capillary and circulating the coolant through the channel, as well as a light source and detector for analyzing the separated solutes, and controls and programming for automated operation. Typically, the instrument will be computer controlled, and will be designed to analyze a multitude of samples in succession, and to identify the separated components of the sample and print out their identification and quantity.

The cartridge is held in the retracted position as shown, and installed into the instrument by insertion in a slot 76. As the cartridge is pushed down inside the slot 76, two spring-mounted release pins 77, 78 are depressed by the cartridge housing. These release pins are in alignment with the catches 54, 55 on the cooling block (FIG. 1), and when contact is made, the release pins depress the catches to clear the upper edge of the housing. The cooling block can then be pushed down inside the housing 13 to extend the exposed capillary ends as well as the capillary mounts and coolant inlet and outlet ports below the housing, thereby making all necessary fluid connections to conduct sample loading and electrophoresis. It will be noted in FIG. 1 that the upper edge 52 of the cartridge housing has a protruding rim 79, but that this rim has two breaks 80, 81 to permit sliding of the housing down beyond the release pins 77, 78, respectively, of the instrument, thereby providing access of the release pins to the catches 54, 55.

Once the cartridge 11 is in place in the slot 76 of the instrument, and all fluid connections are made and the light path of the cartridge is in alignment with the light source 82 of the instrument and the detector (not shown), the cartridge may be secured in place by a pair of rotatably mounted handles 83, 84. To remove the cartridge after use, the handles 83, 84 are rotated upward and outward to clear the cartridge, and the cartridge is removed by grasping the cooling block 12 inside the cut-out section 53 of the housing and pulling upward. This will draw the cartridge into the retracted position to protect the capillary ends prior to removal of the cartridge from the instrument. A recess 85 along a rear wall of the instrument above the slot provides finger access to the cooling block for easy removal.

The components of the invention may be fabricated from conventional materials of construction. The primary consideration is that the materials be electrically insulating. Otherwise, the materials are not critical and can be varied widely.

The foregoing is offered primarily for purposes of illustration. It will be readily apparent to those skilled in the art that modifications of the features shown and described herein, as well as variations thereon and substitutions therefor can be made without departing from the spirit and scope of the invention.

What is claimed is:

1. A capillary cartridge for high performance electrophoresis, comprising:
   a cooling block having an internal coolant flow channel with a capillary coiled therein, the two ends of said capillary passing through capillary mountings on the periphery of said cooling block to define capillary extensions outside of said cooling block, each said capillary mounting sealing around said capillary to prevent leakage of coolant, and a light path extending through said cooling block to permit solute detection through said capillary at a location in proximity to one of said capillary mountings; and
   a housing constructed to receive said cooling block, with ports to permit passage of said capillary extensions, said housing constructed to permit said cooling block to slide therein between an extended position in which said capillary extensions extend outside said housing and a retracted position in which said capillary extensions are retracted inside said housing.

2. A capillary cartridge in accordance with claim 1 further comprising stops limiting the travel of said cooling block at said extended and retracted positions to prevent disengagement of said cooling block from said housing.

3. A capillary cartridge in accordance with claim 1 further comprising spring-loaded means on said cartridge biased to obstruct movement of said cooling block from said retracted position to said extended position.

4. A capillary cartridge in accordance with claim 3 in which said housing receives said cooling block through an opening, and said spring-loaded means are spring-loaded protrusions on said cooling block biased to abut the rim of said opening until depressed by externally applied pressure.

5. A capillary cartridge in accordance with claim 1 further comprising inlet and outlet ports for coolant passage through said coolant flow channel.

6. A capillary cartridge in accordance with claim 1 in which said capillary mountings have gasket members externally secured thereto to form a pressure-retaining seal when exposed to an external elevated pressure.

7. A capillary cartridge in accordance with claim 1 further comprising inlet and outlet ports for coolant passage through said coolant flow channel, and said capillary mountings and said inlet and outlet ports all have gasket members externally secured thereto to form a pressure-retaining seal when exposed to an external elevated pressure.

8. A capillary cartridge in accordance with claim 1 in which said cooling block and said housing are each substantially rectangular with thicknesses relatively small compared to their lengths and widths, said cooling block further comprises coolant ports for inlet and outlet of coolant, said capillary mountings and said coolant ports are all positioned along a first edge of said cooling block, said housing receives said cooling block through an opening along a second edge of said cooling block opposing said first edge, such that said cooling block protrudes from said opening when in said retracted position and is substantially aligned with said first edge when in said extended position.

9. A capillary cartridge in accordance with claim 8 further comprising spring-loaded protrusions on said cooling block biased to abut the rim of said opening and thereby prevent movement of said cooling block from said retracted position to said extended position until depressed by externally applied pressure.

10. A capillary cartridge in accordance with claim 8 in which said second edge of said housing has a central recessed portion exposing a section of said cooling block to permit grasping thereof and thereby pulling of said cooling block from said extended to said retracted position.

11. A capillary cartridge in accordance with claim 1 further comprising opposing windows in said housing positioned to be aligned with said light path when said cooling block is in said extended position.

12. A capillary cartridge in accordance with claim 1 in which said light path is defined by aligned openings in opposing flat faces of said cooling block, each said opening surrounded by a raised cylindrical rim.

13. A capillary cartridge in accordance with claim 1 in which said coolant flow channel is of substantially constant width forming a looped path to accommodate a coiled capillary.

* * * * *